US009572507B2

(12) United States Patent
Moore et al.

(10) Patent No.: US 9,572,507 B2
(45) Date of Patent: Feb. 21, 2017

(54) COMBINATION PHYSIOLOGIC SENSOR

(71) Applicant: DYMEDIX CORPORATION, Shoreview, MN (US)

(72) Inventors: James P. Moore, Bloomington, MN (US); Todd M. Eiken, Lindstrom, MN (US)

(73) Assignee: DYMEDIX CORPORATION, Shoreview, MN (US)

( * ) Notice: Subject to any disclaimer, the term of this patent is extended or adjusted under 35 U.S.C. 154(b) by 160 days.

(21) Appl. No.: 14/482,705

(22) Filed: Sep. 10, 2014

(65) Prior Publication Data
US 2016/0066810 A1 Mar. 10, 2016

(51) Int. Cl.
*A61B 5/0408* (2006.01)
*A61B 5/00* (2006.01)
*A61B 5/113* (2006.01)
*A61B 5/0205* (2006.01)
*A61B 5/08* (2006.01)

(52) U.S. Cl.
CPC ......... *A61B 5/04087* (2013.01); *A61B 5/6823* (2013.01); *A61B 5/0205* (2013.01); *A61B 5/0809* (2013.01); *A61B 5/1135* (2013.01); *A61B 5/4818* (2013.01); *A61B 2560/0412* (2013.01); *A61B 2562/0209* (2013.01); *A61B 2562/06* (2013.01); *A61B 2562/164* (2013.01)

(58) Field of Classification Search
CPC ... A61B 5/0809; A61B 5/1135; A61B 5/4818; A61B 5/6823; A61B 5/0205; A61B 5/04087; A61B 2560/0412; A61B 2562/06; A61B 2562/164; A61B 2562/0209

USPC .................. 600/300, 301, 300.301
See application file for complete search history.

(56) References Cited

U.S. PATENT DOCUMENTS 4,180,059 A 12/1979 Tiep
4,909,260 A 3/1990 Salem et al.
5,316,010 A 5/1994 Brown
(Continued)

FOREIGN PATENT DOCUMENTS

DE WO 2009074928 A1 * 6/2009 ......... A61B 5/04085

OTHER PUBLICATIONS

Murphy et al., "An Innovative Piezoelectric-Based Method for Measuring Pulse Wave Velocity in Patients With Hypertension", The Journal of Clinical Hypertension, Jul. 2011, vol. 13, No. 7, pp. 497-505.
(Continued)

*Primary Examiner* — Gary Jackson
*Assistant Examiner* — Boniface N Nganga
(74) *Attorney, Agent, or Firm* — Nikolai & Mersereau, PA; Thomas J. Nikolai

(57) ABSTRACT

A multi sensor module especially designed for use in sleep-study applications includes a PVDF film piezoelectric transducer enclosed between an upper layer of a single-sided adhesive tape strip and a lower layer of a double-sided adhesive tape strip. Also adhesively affixed to the upper single-sided adhesive tape strip, but not overlaid by the lower double-sided adhesive tape strip are first and second conductive electrodes. The combination sensor module is adapted to be adhesively affixed to the chest area of a person and further included in an extension of the PVDF strip that is adapted to overlay the suprasternal notch of a person for producing signals responsive to respiratory activity of the person.

1 Claim, 2 Drawing Sheets

(56) References Cited

U.S. PATENT DOCUMENTS

| | | | |
|---|---|---|---|
| 6,445,942 | B1 | 9/2002 | Berthon-Jones et al. |
| 6,491,642 | B1 * | 12/2002 | Stasz .................... A61B 5/0816 |
| | | | 600/529 |
| 6,547,743 | B2 | 4/2003 | Brydon |
| 6,984,207 | B1 | 1/2006 | Sullivan et al. |
| 7,797,043 | B1 | 9/2010 | Dupelle et al. |
| 8,147,407 | B2 | 4/2012 | Moore et al. |
| 2008/0312524 | A1 | 12/2008 | Solosko et al. |
| 2010/0076251 | A1 * | 3/2010 | Stasz ....................... A61B 5/08 |
| | | | 600/28 |
| 2012/0071731 | A1 * | 3/2012 | Gottesman ............. A61B 5/486 |
| | | | 600/301 |
| 2012/0101399 | A1 | 4/2012 | Henderson |

OTHER PUBLICATIONS

Van Surell et al., "Evaluation of an Ambulatory Device, CID 102, in the Diagnosis of Obstructive Sleep Apnoea Syndrome", European Respiratory, May 1995, vol. 8, No. 5, pp. 795-800.

\* cited by examiner

COMBINATION PHYSIOLOGIC SENSOR

CROSS REFERENCE TO RELATED APPLICATIONS

None

RELATED GOVERNMENT RESEARCH

None

BACKGROUND OF THE INVENTION

I. Field of the Invention

This invention relates generally to physiologic sensors, and more particularly to a sensor module which when affixed to a person's chest will provide information related to respiratory effort, cardiac rhythm and sleep apnea.

II. Discussion of the Prior Art

In conducting a sleep study on a patient, it is customary to append a plurality of sensors to the patient for measuring and recording a number of physiologic parameters including, but not limited to, rapid eye movement, electric myograph (EMG), electrocardiograph (ECG), respiratory air flow, respiratory effort, cardiac rhythm, leg twitches, etc. Typically, individual sensors will be placed on the head, face, chest, abdomen and legs. The sensors typically have elongated electrical wire leads for connection to electronic display and recording modules. With all of these wires involved, it is often difficult for a patient to sleep comfortably, especially to be able to periodically roll over in bed. In addition, to monitor respiratory effort, it is the practice to affix respiratory effort belts about the chest and/or abdomen that must be snug to prevent the belt from slipping out of place. This too is inimical to patient comfort.

It is accordingly a principle object of the present invention to provide a sensor module for use in sleep study applications that combines plural sensors into a single package that when appropriately placed and adhered to a patient's skin allows plural parameters to be monitored and/or recorded. As such, the sensor leads can be combined in a single cable that can be more readily routed in a way that interferes less with a patient's ability to shift positions. Moreover, the use of effort belts is avoided.

SUMMARY OF THE INVENTION

The present invention comprises a multi-sensor module that has a flexible strip of PVDF polymer of a predetermined length and width dimension having a coating of metal on opposed major surfaces and first and second insulated electrical leads conductively and individually connected at a distal end to the metal coatings. Laterally spaced from opposed ends of the flexible strip of PVDF polymer are first and second conductive electrodes that are substantially coplanar with the strip of PVDF polymer. Third and fourth insulated electrical leads conductively and individually are connected to the first and second conductive electrodes. The multi-sensor module further comprises an elongated strip of a single-sided adhesive tape whose length and width dimensions both exceed the length and width dimensions of the strip of PVDF polymer and sufficient to overlay the first and second conductive electrodes. Completing the assembly is an elongated strip of a double-sided adhesive tape arranged such that one side of the double-sided adhesive tape adheres to an adhesive on the strip of single-sided adhesive tape with the strip of PVDF polymer, but not the first and second conductive electrodes, sandwiches there between.

In accordance with a further embodiment, the strip of PVDF polymer is generally T-shaped. With a leg of the T projecting generally perpendicularly to the length dimension of the PVDF strip for a predetermined distance sufficient to reach the sub-sternal notch of a patient when the strip of double-sided adhesive tape is adhered to the patient's midline chest area.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
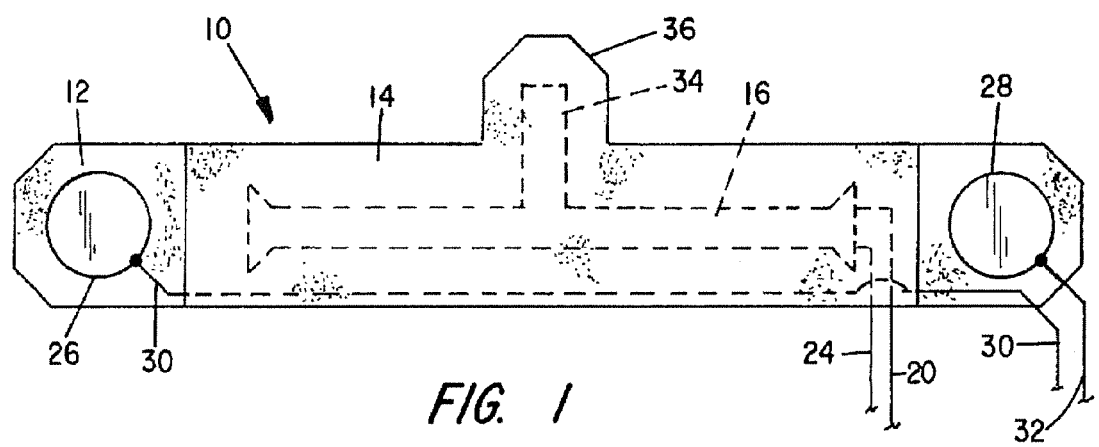
FIG. 1 is a bottom plan view of a preferred embodiment of the present invention.
Figure 2:
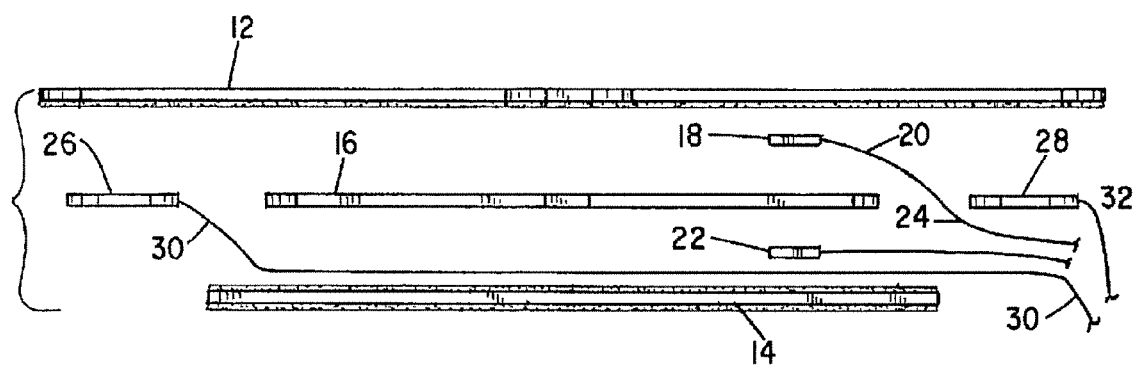
FIG. 2 is an exploded side view of the embodiment of FIG. 1.
Figure 3:
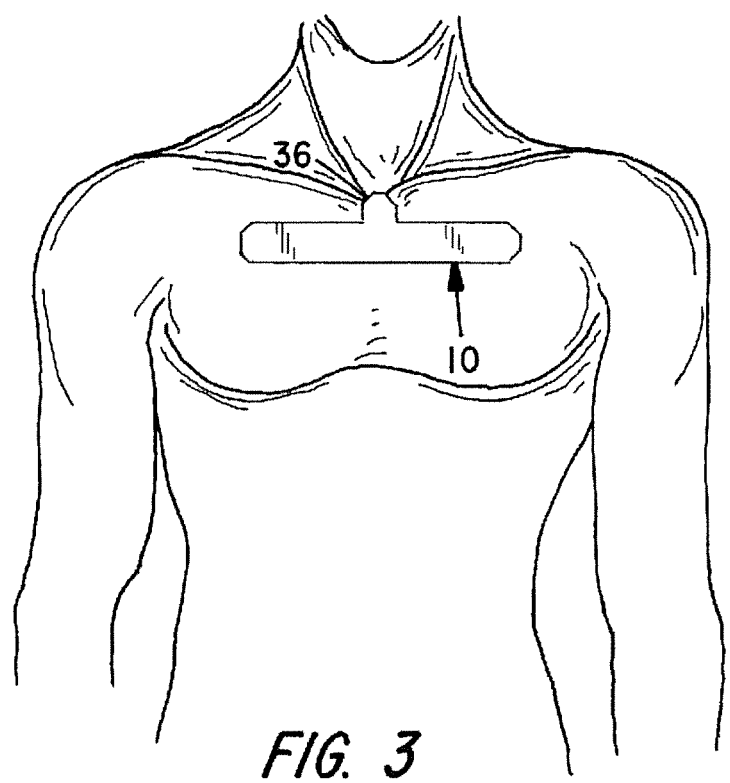
FIG. 3 shows the sensor module of FIG. 1 appended to a human's midline chest area.

Referring to the drawings, the combination physiologic sensor is indicated generally by numeral 10 and is seen to comprise a strip 12 of a single-sided adhesive tape and a strip 14 of a double-sided adhesive tape and with a strip of a PVDF polymer 16 sandwiches there between. The polymer strip 16 has a thin layer of metallization on opposed major surfaces thereof and conductively attached to the metallization layer on the upper surface of the polymer strip 16 is a terminal pad 18 having an elongated insulated lead 20 conductively attached at its distal end to the pad 18. Likewise, a terminal pad 22 is conductively affixed to the metallization layer on the lower surface of the polymer strip 16 and an elongated lead 24 has its conductor wire attached at its distal end to the pad 22.

Affixed by the adhesive on the single-sided tape strip 12 are first and second conductive electrodes 26 and 28 each with an insulated electrical lead 30, 32 conductively attached thereto. It is to be noted that the strip 14 of double-sided adhesive tape only overlays the PVDF polymer strip 16 and not the electrodes 26 and 28.

As seen in FIG. 1, the metallized PVDF polymer strip 16 is generally T-shaped having a leg portion 34 projecting normally from the strip 16 and both the upper single-sided adhesive strip 12 and the lower double-sided adhesive tape strip 14 is cut so as to include a projection as at 36 that sandwiches the leg 34 there between.

Prior to use, the adhesive on the upper layer 12 and lower layer 14 is protected by a release paper sheet that is readily removable at the time of use without damage to the adhesive layers. In use, the release paper sheet is removed and the sensor module is made to adhere to the patient's skin on the upper midline chest area and with the leg 34 of the PVDF polymer strip overlaying the person's suprasternal notch. As the person inhales, chest expansion will result in a stretching force being applied to the PVDF polymer. Likewise, upon exhalation, the stretching force is removed. In that the PVDF film exhibits piezoelectric properties, a voltage signal will be developed between the terminal pads 18 and 22 and delivered over the leads 20 and 24 to a suitable electronics module (not shown) for storage and/or display. The conductive electrodes 26 and 28 will be in direct contact with the person's skin for sensing cardiac activity and also can be used to generate impedance pneumography waveforms. Furthermore, as the leg 34 overlays the suprasternal notch, signals emanating there from can be used to sense breathing disorders such as obstructive sleep apnea/hypopnea, snoring and periodic breathing. These signal components differ in frequency and are readily isolated using known filtering techniques.

In that the leads 20, 24, 30, 32 can comprise strands of a cable, they can be brought out to the electronic monitor and connect to appropriate input jacks, thus avoiding the need to route individual strands from individual electrodes. Without limitation, the powder adhesive strip 12 may be in a range from 6 to 12 inches depending upon the age and sex of the person while the width of the strip 12 may be from 1 to 2 inches.

It is to be understood that the description of the various embodiments is merely exemplary in nature and, thus, variations that do not depart from the gist of the example and desired description herein are intended to be within the scope of the present disclosure. Such variations are not to be regarded as a departure from the spirit and the scope of the present disclosure.

What is claimed is:

1. A multi-sensor module comprising:
a) a flexible strip of polyvinylidene fluoride (PVDF) polymer of a predetermined length and width dimension and being T-shaped with a leg of the T projecting out from the length dimension of the PVDF strip for a predetermined distance having a coating of metal on opposed major surfaces with first and second insulated electrical leads conductively and individually connected at one end of the strip to the metal coatings;
b) first and second conductive electrodes coplanar with and spaced longitudinally from opposed ends of the flexible strip of PVDF polymer with third and fourth insulated electrical leads conductively and individually connected to the first and second conductive electrodes;
c) an elongated T-shaped strip of a single-sided adhesive tape whose length and width dimensions both exceed the length and width dimension of the strip of PVDF polymer and sufficient to overlay the first and second conductive electrodes with a leg of the T on the T-shaped single sided adhesive tape overlaying the leg of the T-shaped strip of polymer; and
d) an elongated strip of a double-sided adhesive tape arranged such that one side of the double-sided adhesive tape adheres to an adhesive on the T-shaped strip of single-sided adhesive tape with the T-shaped strip of PVDF polymer but not the first and second conductive electrodes, disposed there between and wherein the predetermined distance is adapted to reach the suprasternal notch of a patient when the strip of double-sided adhesive tape is adhered to the patient's midline chest area.

* * * * *

UNITED STATES PATENT AND TRADEMARK OFFICE
CERTIFICATE OF CORRECTION

PATENT NO. : 9,572,507 B2
APPLICATION NO. : 14/482705
DATED : February 21, 2017
INVENTOR(S) : Moore et al.

Page 1 of 1

It is certified that error appears in the above-identified patent and that said Letters Patent is hereby corrected as shown below:

In the Specification

Column 2, Line 7, delete the word "sub-sternal" and insert the word --suprasternal--

Signed and Sealed this
Eleventh Day of August, 2020

Andrei Iancu
*Director of the United States Patent and Trademark Office*